United States Patent [19]

Hill et al.

[11] Patent Number: 5,730,967

[45] Date of Patent: Mar. 24, 1998

[54] ULTRAMULSION BASED SKIN CARE COMPOSITIONS

[75] Inventors: Ira D. Hill, Locust; Peter P. Walters, Neshanic, both of N.J.; Dale G. Brown, Wharton, Tex.

[73] Assignee: WhiteHill Oral Technologies, Inc., Chadds Ford, Pa.

[21] Appl. No.: 462,600

[22] Filed: Jun. 5, 1995

[51] Int. Cl.$^6$ ........................................... A61K 31/74
[52] U.S. Cl. ..................... 424/78.01; 252/312; 252/308; 252/314
[58] Field of Search ................. 424/78.01; 252/312, 252/308, 314

[56] References Cited

U.S. PATENT DOCUMENTS

| | | | |
|---|---|---|---|
| 2,356,205 | 4/1944 | Blair et al. | 252/8.55 |
| 2,438,091 | 3/1948 | Lynch | 260/482 |
| 2,528,378 | 10/1950 | Mannheimer et al. | 260/309.6 |
| 2,658,072 | 11/1953 | Kosmin | 260/513 |
| 2,826,511 | 3/1958 | Messinger | 117/69 |
| 2,826,551 | 3/1958 | Green | 252/89 |
| 3,254,714 | 6/1966 | Gogarty et al. | 166/9 |
| 3,307,628 | 3/1967 | Sena | 166/9 |
| 3,433,780 | 3/1969 | Cekada et al. | 260/29.2 |
| 3,497,006 | 2/1970 | Jones et al. | 166/273 |
| 3,506,070 | 4/1970 | Jones | 166/273 |
| 3,964,500 | 6/1976 | Drakoff | 132/7 |
| 3,975,294 | 8/1976 | Dumoulin | 252/354 |
| 4,146,499 | 3/1979 | Rosano | 252/186 |
| 4,152,416 | 5/1979 | Spitzer et al. | 424/46 |
| 4,343,785 | 8/1982 | Schmolka | 424/49 |
| 4,364,817 | 12/1982 | Anderson et al. | 208/8 |
| 4,364,837 | 12/1982 | Pader | 252/173 |
| 4,465,663 | 8/1984 | Schmolka | 424/62 |
| 4,476,107 | 10/1984 | Schmolka | 424/49 |
| 4,511,563 | 4/1985 | Schmolka | 514/162 |
| 4,620,878 | 11/1986 | Gee | 106/287 |
| 4,911,927 | 3/1990 | Hill et al. | 424/443 |
| 4,922,603 | 5/1990 | Kosmowski | 29/568 |
| 4,939,179 | 7/1990 | Cheney et al. | 514/789 |
| 4,942,034 | 7/1990 | Hill et al. | 424/401 |
| 4,950,479 | 8/1990 | Hill et al. | 424/49 |
| 5,009,881 | 4/1991 | Hill et al. | 424/49 |
| 5,032,387 | 7/1991 | Hill et al. | 424/49 |
| 5,057,306 | 10/1991 | Hill et al. | 424/49 |
| 5,057,307 | 10/1991 | Hill et al. | 424/49 |
| 5,057,308 | 10/1991 | Hill et al. | 424/52 |
| 5,057,309 | 10/1991 | Hill et al. | 424/52 |
| 5,057,310 | 10/1991 | Hill et al. | 424/52 |
| 5,098,711 | 3/1992 | Hill et al. | 424/401 |
| 5,165,913 | 11/1992 | Hill et al. | 424/49 |
| 5,284,648 | 2/1994 | White et al. | 424/49 |
| 5,538,667 | 7/1996 | Hill et al. | 252/312 |

FOREIGN PATENT DOCUMENTS 849433  9/1960  United Kingdom.

OTHER PUBLICATIONS

Becher P. in "Emulsions, Theory & Practice", (P.Becher, Ed.) p. 2, Rheinhold, New York, 1965.
Clayton, W., "The Theory of Emulsions and Their Technical Treatment", 4th Ed. p. 1, the Blakiston Co., Philadelphia, 1943.
Bancroft W.D., J. Phy. Chem., 17:501 (1913).
Prince, L.M. in "Microemulsion Theory & Practice", p. 2, Academic Press Inc., New York, NY (1977).
Prince, L.M. in "Biological Horizons in Surface Science", p. 361, Academic Press, Inc. (1973).
Eur. Poly. J., 26:654 (1990).
J. Chem. Phys., 49:1398 (1965).
J. Chem. Phys., 54:5011 (1971).
J. Chem. Phys., 59: 3852 (1973).
Macromolecules, 7:229 (1974).
Macromolecules, 11:627 (1978).
W.Noll, "Chemistry and Technology of Silicones", pp. 428–431 (1968).
Journal of Society of Cosmetic Chemists, 25:609–619 (1974).
Journal of Colloid & Interface Science, 44:242–248 (19723).
"Annals of the New York Academy of Science", Shulman & Montagne (1961).
Rowe et al., Journal of Industrial Hygiene, 30(6): 332–352 (1958).
Calandra et al., ACS Polymer Preprints, 17: 1–4 (1976).
Kennedy et al., J. Toxicol & Environmental Health, 1:909–920 (1976).

*Primary Examiner*—Margaret W. Glass
*Attorney, Agent, or Firm*—Ernest V. Linek

[57] ABSTRACT

The present invention relates to various skin care products including cosmetics, over-the-counter (OTC) and prescription (R) drugs containing, stable, dispersions of certain high viscosity silicones in certain surfactants; wherein:

a. the dispersed silicones, which are insoluble in said surfactant, are oriented by the surfactant such that when dispersed in water they are particularly adept at forming oriented, coatings on skin with enhanced substantivity, and b. the particle size of the dispersed silicone is from between about 0.1 and about 10 microns, with a particle size distribution such that from between about 80 and 95% of the dispersed silicone is within this particle size range. These stable dispersions are described as ULTRAMULSION™ dispersions, which, together with their physical properties, when contained in skin care products, provide these skin care products with distinctive, moisturizing, protecting, healing etc. properties where the non continuous silicone phase functions as a reservoir for various skin treatment substances.

7 Claims, 3 Drawing Sheets

5,730,967

ULTRAMULSION BASED SKIN CARE COMPOSITIONS

BACKGROUND OF THE INVENTION

The present invention relates to unique skin care compositions containing a dispersion of certain silicones in certain surfactants. When added to water these dispersions are stable and are distinct from solutions, emulsions and microemulsions. These dispersions are referred to hereinafter as ULTRAMULSION™ dispersions. This trademark is the property of Whitehill Oral Technologies, Inc. For further information regarding ULTRAMULSION™ dispersions, see copending application Ser. No. 08/144,778, now U.S. Pat. No. 5,538,667, the disclosure of which is hereby incorporated herein by reference. See also copending patent application Ser. Nos. 08/462,613; 08/462,203; 08/463,010; 08/461,698; 08/464,403; 08/462,599; and 08/462,930 now U.S. Pat. No. 5,645,841; all filed on Jun. 5, 1996, the disclosures of which are hereby incorporated by reference.

The ULTRAMULSION™ dispersion based skin care products of the present invention exhibit unique and unexpected substantivity to skin while providing a reservoir for various lipid or oil soluble skin treatment ingredients resulting in healing, moisturizing, protecting, etc. benefits that last on the skin for extended periods. This combination of enhanced substantivity and the reservoir effect described in detail below are further combined with excellent particle size which results in unique coatings which have a broad range of uses in skin care.

The uniqueness and novelty of the ULTRAMULSION™ dispersion based skin care products of the present invention are more readily appreciated when these products are compared to other skin care products.

ULTRAMULSION™ dispersion based skin care products of the present invention include a wide range of products applied as coatings to the skin including:

a. creams and lotions such as described in U.S. Pat. No. 4,939,179, moisturizers, wrinkle treatments, bath products, makeup removers, night creams, fragrances, baby products;

b. underarm care products including deodorants and antiperspirants in spray, cream, roll-on and stick form. See for example, U.S. Pat. No. 4,922,603;

c. soaps including liquid "soft soap" and bar soaps with and without antimicrobials such as triclosan;

d. skin products such as sunscreens, insect repellents, surgical scrubs;

e. shaving products including shaving creams, depilatories and after shave products;

f. skin treatments including burn treatment, analgesics, antiseptics, dermatitis and psoriasis treatments, drying-antihistaminic lotions, bedsore treatments, healants, acne treatments, debriding treatments;

g. medicinal ointments including aloe, vitamin E, wound dressings, soaks, salves, ointments, h. lip balms, massage products, and the like.

Silicone coating compositions have been disclosed in a number of different publications. Such publications include U.S. Pat. No. 2,826,511 to Green; U.S. Pat. No. 3,964,500 to Drakoff; U.S. Pat. No. 4,364,817 to Pader; and British Patent No. 849,433 to Woolston. While these patents disclose silicone containing compositions, they also do not provide answers to many of the problems encountered in making a totally satisfactory silicone based product.

The ULTRAMULSION™ dispersions of the present invention are distinct from other emulsions as will become apparent from the following:

When a system consists of a single liquid phase it is described as a solution. A system containing two or more liquid phases is described as a multiphase solution or emulsion.

According to Becher, an emulsion is an unstable heterogeneous system in which the diameters of the dispersed droplets in general exceed 1000 Å. Becher P. in "Emulsions, Theory & Practice", (P. Becher, Ed.) page 2, Rheinhold, New York, 1965.

A more comprehensive definition of emulsion is advanced by Clayton: "An emulsion is a system containing two liquid phases, one of which is dispersed as globules in the other. The liquid which is broken up into globules is termed the dispersed or discontinuous phase, while the liquid surrounding the globules is known as the continuous phase or dispersing medium" Clayton, W., "The Theory of Emulsions and Their Technical Treatment", 4th Ed. page 1, the Blakiston Co., Philadelphia, 1943. It is well accepted that, mechanical work is required to effect such an emulsion, see Bancroft W. D., *J. Phys. Phy. Chem.*, 17: 501 (1913).

According to Prince, an emulsion may be defined as a dispersion of two (or more) mutually insoluble liquids, one in the other. Because of the surface tension forces at play between the two liquids, the dispersed phase consists of spherical droplets. Prince, L. M. in "Microemulsion Theory & Practice", pg. 2, Academic Press Inc., New York, N.Y. (1977). See also Prince, L. M. in "Biological Horizons in Surface Science", pg. 361, Academic Press, Inc. (1973).

Emulsions, are generally not stable and upon standing or after centrifuging tend to separate into two or more liquid layers.

The three definitions of emulsions set forth above share one common attribute, that is, mechanical work must be put into the emulsions described in order to disperse one liquid in the other in the form of droplets. This mechanical work can be in the form of agitation, homogenization, ultrasonication, etc.

In contrast, dispersions of very small droplet sizes which are formed spontaneously without the input of any mechanical work are called microemulsions. See Prince 1977, p. 3. Generally, two surfactants are used in forming microemulsions, i.e., a water soluble surfactant and a co-surfactant such as alcohol, where one phase of the microemulsion is generally water. Thus, dilution or adulteration of the dispersed phase by the co-solvent generally accompanies microemulsion formation. The ratio of surfactant to dispersed phase in microemulsions is much higher than that of emulsions. Microemulsions are further characterized as optically clear or opalescent and when spun in a laboratory centrifuge for 5 minutes at 100 G's, the dispersion remains stable and does not separate.

Thus, fine particle sizes, exceptional stability and rheological properties that can be easily adjusted, distinguish microemulsions from emulsions. Moreover, to date, no microemulsions have appeared in which one of the mutually insoluble liquids is not water. See Prince, page 34, (1977).

It has been surprisingly found that certain ULTRAMULSION™ dispersions, i.e., those of the present invention, provide various skin care products with improved moisturizing, protecting, repairing, etc, attributed to their enhanced substantivity and the reservoir effect achieved by solubilizing various lipid soluble substances in the discontinuous silicone phase of the ULTRAMULSION™ dispersion.

It is an object of the present invention to provide ULTRAMULSION™ dispersion based skin care products with enhanced substantivity and containing a reservoir of various ingredients for moisturizing, protecting, healing, etc. skin.

It is a further object of the present invention to provide ULTRAMULSION™ dispersion based skin care products wherein various lipid soluble actives are released from the ULTRAMULSION™ dispersion coating onto the skin over an extended period.

It is another object of the invention to provide a method for manufacturing the ULTRAMULSION™ dispersion based skin care products of the invention.

It is still another object of the invention to provide means for treating, moisturizing, protecting, etc. skin with ULTRAMULSION™ dispersion based skin care products.

It is a further object of the present invention to provide ULTRAMULSION™ dispersion based skin care products wherein various lipid or oil soluble actives are released from the ULTRAMULSION™ dispersion coating onto the skin over an extended period.

It is also an object of this invention to provide an ULTRAMULSION™ dispersion for water based skin care products without the need to resort to use of complex high energy processes.

These and other objects will become readily apparent from the detailed description which follows.

Unless otherwise indicated, all percentages and ratios herein are by weight.

SUMMARY OF THE INVENTION

As described above, the present invention relates to various skin care products containing stable dispersions of certain high viscosity silicones in certain surfactants; wherein:

a. the dispersed silicones, which are insoluble in said surfactant, are oriented by the surfactant such that when dispersed in water they are particularly adept at forming oriented coatings on skin with enhanced substantivity, and b. the particle size of the dispersed silicone is from between about 0.1 and about 10 microns, with a particle size distribution such that from between about 80 and 95% of the dispersed silicone is within this particle size range. In certain embodiments, between 80–95% of two dispersed silicones is less than 1–2 microns in particle size. These stable dispersions are described as ULTRAMULSION™ dispersions, which, together with their physical properties, when contained in skin care products, provide these skin care products with distinctive treating, moisturizing, protecting, etc. properties where the non continuous silicone phase functions as a reservoir for various skin treatment substances.

The ULTRAMULSION™ dispersions of skin care products of the present invention combine certain characteristics of emulsions with certain features of microemulsions. That is, like emulsions, they are two phase systems comprising a silicone dispersed in a continuous, surfactant phase, wherein the silicone is insoluble in the surfactant. Unlike emulsions, but like microemulsions, these dispersions are stable. Unlike microemulsions, but like emulsions, mechanical work is required to form ULTRAMULSION™ dispersions. Unlike microemulsions, but like emulsions, these ULTRAMULSION™ dispersions are not formed spontaneously. Like emulsions, the ULTRAMULSION™ dispersions do not contain a cosolvent commonly found in microemulsions. Of course, the ULTRAMULSION™ dispersions of the present invention can be dispersed in various liquids such as water as stable dispersions.

These dispersions of ULTRAMULSION™ dispersions in water have excellent utility in various skin care products. See various examples below.

While not wishing to be bound by theory, it is hypothesized that unlike either emulsions or microemulsions, the dispersed silicones of the ULTRAMULSION™ dispersions of the present invention are oriented with their polar moieties in one general plane and their hydrophilic moieties in a plane approximately opposite that of the polar moieties. This orientation promotes stability as well as bonding between the polar or hydrophilic moieties and the skin substrate thereby effecting oriented, monolayer coatings of the silicone onto skin. These oriented dispersions of silicones have a broad range of utility in skin care as detailed in the various examples below.

The emulsifying effects of uncoiling of the silicone molecule with the oxygen moieties generally oriented in one plane distinct from that of the organo moieties as illustrated in FIGS. 1 and 2 are further substantiated by the following references: *Eur. Poly. J.*, 26: 654 (1990); *J. Chem. Phys.*, 49: 1398 (1965); *J. Chem. Phys.*, 54: 5011 (1971); *J. Chem. Phys.*, 59: 3825 (1973); *Macromolecules*, 7: 229 (1974); *Macromolecules*, 11: 627 (1978) and "Rubber-Like Elasticity: A Molecular Primer", J. Mark, New York, Wiley-Interscience, 1988.

Methods of preparing polyorganosiloxane emulsions with an average particle size of less than about 0.3 microns and polyorganosiloxane microemulsions with an average particle size of less than about 0.14 micron are described in U.S. Pat. No. 4,620,878. Preparation of oil-in-water microemulsions are described in U.S. Pat. No. 4,146,499. Specific surface active compositions used as emulsifiers with diorganopolysiloxanes to form transparent microemulsions are described in U.S. Pat. Nos. 4,0562,331 and 3,975,294. U.S. Pat. No. 3,433,780 teaches the preparation of colloid silane suspensions. See also "Chemistry and Technology of Silicones", W. Noll, pp. 428 to 431 (1968); *Journal of Society of Cosmetic Chemists*, 25: 609–619 (1974) and *Journal of Colloid & Interface Science*, 44: 242–248 (1973).

Micellar dispersions, microemulsions, transparent emulsions, etc. are described in detail in "Annals of the New York Academy of Science", Shulman & Montagne (1961); U.S. Pat. No. 2,356,205, "The Theory of Emulsions & Their Technical Treatment", 5th Edition, 1954, U.S. Pat. Nos. 3,497,006; 3,506,070, 3,254,714 and 3,307,628.

The aqueous-free ULTRAMULSION™ dispersions of silicones in surfactants as described herein are neither taught nor suggested by the foregoing references.

For the purposes of the present invention:

a. stable is defined as follows; a dispersion of the ULTRAMULSION™ dispersion in water when subjected to centrifuging in a 100 G environment for 5 minutes, less than about 10% by weight of the ULTRAMULSION™ dispersion separates from the continuous water phase and/or a substantial portion (i.e., >50%) of the dispersed phase resists separation. This latter definition is particularly applicable to higher viscosity silicones. See Table 2.

b. water-free means, that the ULTRAMULSION™ dispersion of silicone and surfactant is substantially free from water.

c. solvent free means, that the ULTRAMULSION™ dispersion of silicone and surfactant is substantially free from co-solvents such as ethanol, isopropanol, and the like.

d. oriented means, that the polar moieties of the "uncoiled" polydimethylsiloxane in the ULTRAMULSION™ dispersion are generally aligned in one plane with the hydrophilic oil seeking moieties aligned in a second plane such as illustrated in FIG. 2.

e. monolayer means, that a monomolecular film of the ULTRAMULSION™ dispersion of the present invention when dispersed in water is attracted to skin by secondary bonding force to form a substantive coating thereon.

DETAILED DESCRIPTION OF THE PREFERRED EMBODIMENTS

Figure 1:
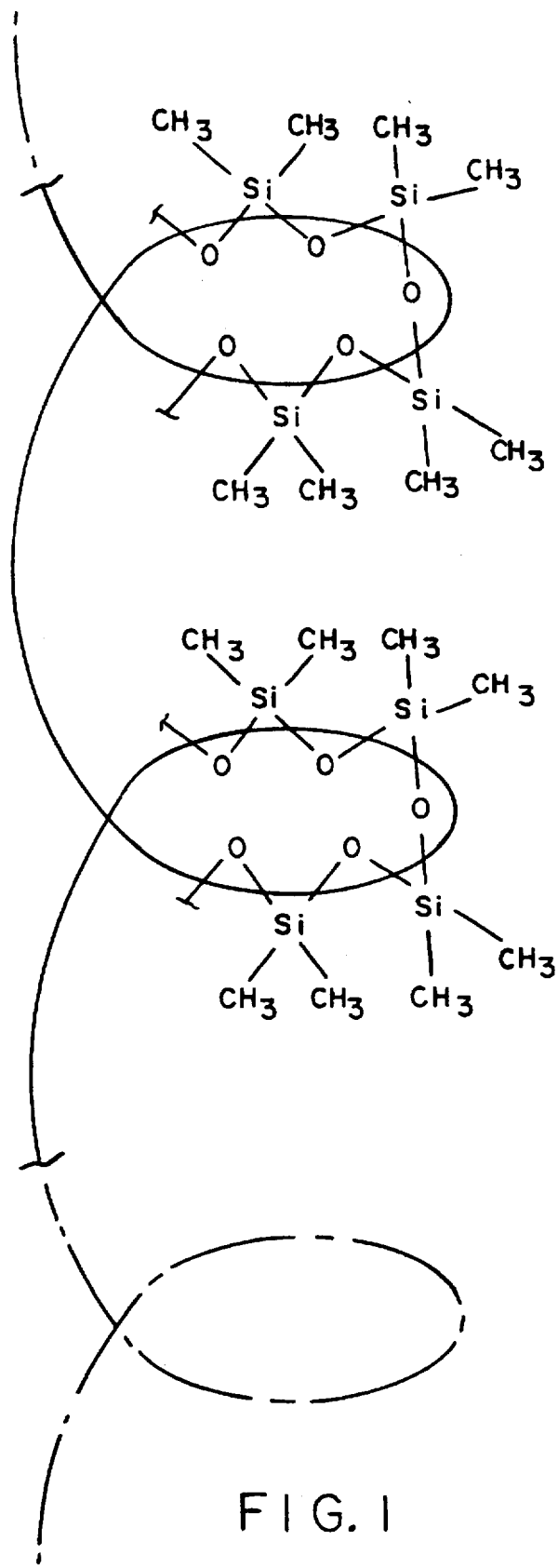
FIG. 1 illustrates the "coiled" molecular configuration of polydimethylsiloxanes.

Referring to the drawings, FIG. 1 illustrates the accepted "coiled" configuration advanced for polydimethylsiloxanes, wherein the methyl moieties are oriented outward while the oxygen moieties are oriented inward towards the axis of the coil or helix. This configuration does not readily promote "bonding" between the oxygen moieties and compatible surfaces, such as skin.

Figure 2:
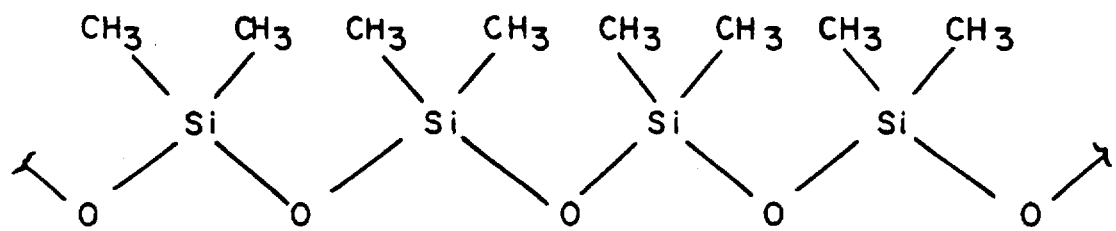
FIG. 2 illustrates the molecular configuration of oriented polydimethylsiloxanes after ULTRAMULSION™ dispersion processing.

FIG. 2 illustrates the "uncoiled oriented" configuration proposed for polydimethylsiloxanes that have been dispersed in the stable, ULTRAMULSION™ dispersions of the present invention, wherein the oxygen moieties are generally oriented in one plane distinct from that of the methyl moieties. This proposed uncoiled oriented configuration appears to support the unique and unexpected "bonding" and enhanced substantivity properties of the ULTRAMULSION™ dispersions of the present invention to skin, as evidenced by the various ULTRAMULSION™ dispersion based skin care products described in the examples below.

Figure 3:
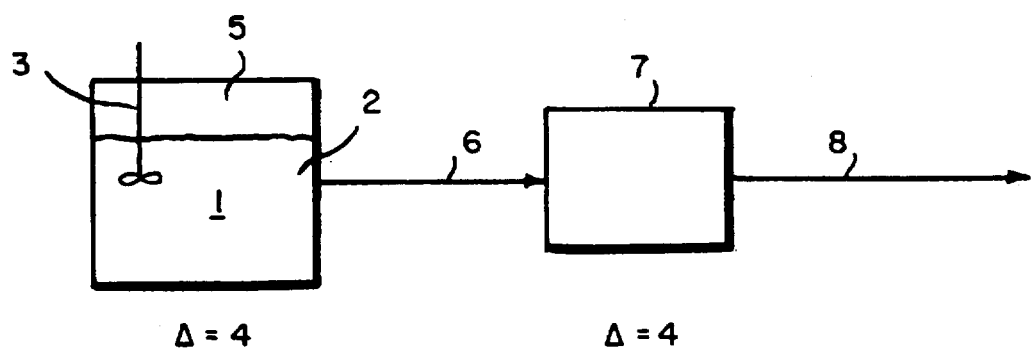
FIG. 3 illustrates schematically an ULTRAMULSION™ dispersion process of the invention.

FIG. 3 illustrates the ULTRAMULSION™ dispersion process of the present invention wherein a surfactant and a polydimethylsiloxane 1, substantially free from water and co-solvent, are mixed in vessel 2, provided with mixing means 3, heat source 4, and inert head space 5. The heated and mixed surfactant/polydimethylsiloxane 6, is then subjected to high shear dispersion at an elevated temperature in dispersing means 7, to produce the ULTRAMULSION™ dispersion 8, of the invention.

Figure 4:
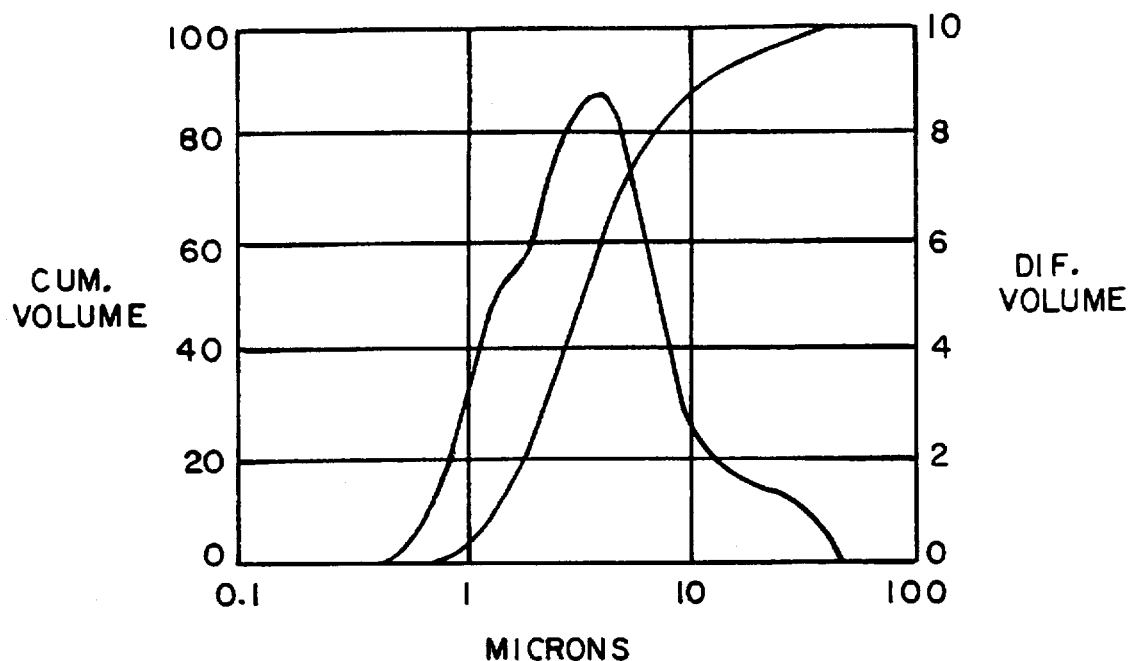
FIGS. 4 and 5 illustrate that the ULTRAMULSION™ dispersions of the invention produced via various high shear dispersing means having particle size distribution of 80+% under 10 microns.

FIG. 4 is a chart describing the particle size distribution of an ULTRAMULSION™ dispersion of the present invention containing from about 50 to 95% by weight nonionic surfactant and from about 5 to 50% by weight polydimethylsiloxane (2.5 million cs) produced in a continuous process with an IKA Works dispersing means, (high shear dispersing) with an inlet temperature of 140° C. and an outlet temperature of 210° C.

Figure 5:
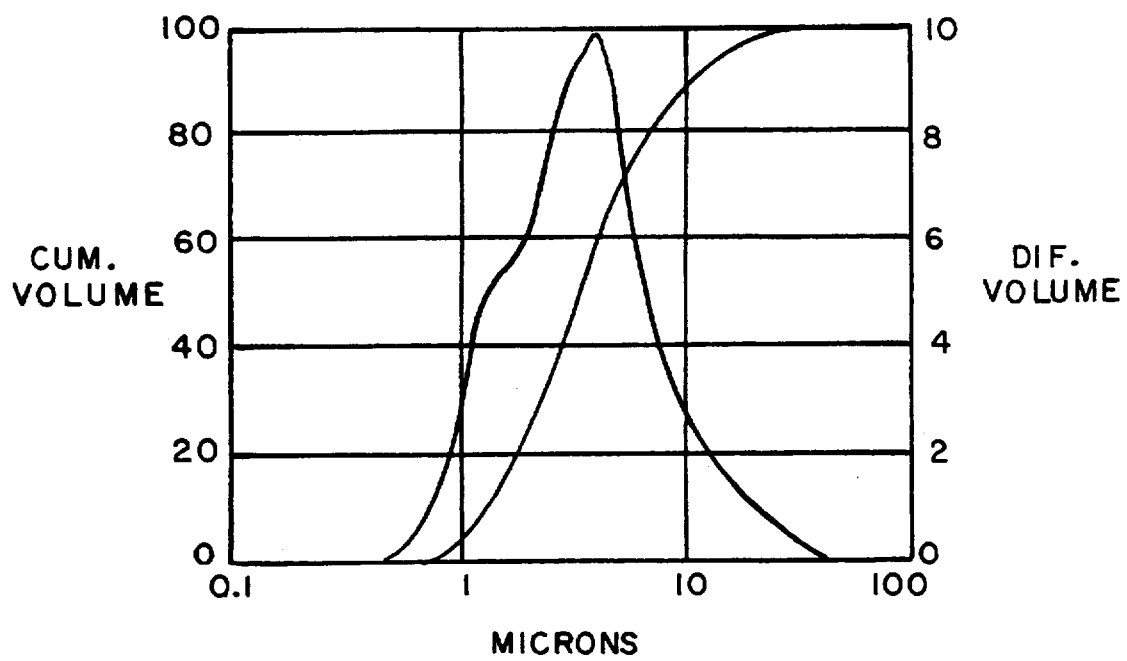

FIG. 5 is a chart describing the particle size distribution of an ULTRAMULSION™ dispersion of the present invention containing from about 50 to 95% by weight nonionic surfactant and from about 5 to 50% by weight polydimethylsiloxane (2.5 million cs) produced in a batch process with a Ross M/E 100 LC dispersing means fitted with a 20 mesh screen, operated at a temperature from about 120° to 160° C.

For purposes of the present invention, the term silicone means a clear, colorless substance containing polydialkylsiloxane polymers with average kinematic viscosities ranging from about 100,000 centistokes (cs) to about 50 million cs, preferably from about 1 million cs to about 25 million cs, more preferably from about 1.5 million cs to about 10 million cs, and most preferably from about 2 million to about 5 million cs. This definition intentionally includes the so-called "gum" silicones having viscosities of 30 to 50 million cs. Certain high viscosity polydimethylsiloxanes having viscosities from about 2.5 million cs to about 4 million cs are particularly preferred for the skin care products of the present invention. Other polydimethylsiloxanes suitable for the present invention include "substituted" water insoluble silicones and mixtures of polydiorganosiloxanes and substituted water insoluble silicones. Specifically, water soluble silicones are excluded from the ULTRAMULSION™ dispersions of the present invention. See also Tables 1 and 2 below.

The viscosity of some silicones can be measured by means of a glass capillary viscometer as set forth in Dow Corning Corporate Test Method CTM0004, Jul. 20, 1970.

The silicone may be either a high viscosity polyalkyl siloxane as described in detail below, a polyaryl siloxane, a polyalkylaryl siloxane or a polyether siloxane copolymer. Mixtures of these silicones may also be used and are preferred in certain embodiments of the present invention.

The polyalkylaryl siloxanes that may be used include, for example, polymethylphenylsiloxanes having viscosities above 1 million centistokes at 20° C. Some of these siloxanes are available, for example, from the General Electric Company or from Dow Corning.

The polyether siloxane copolymer that may be used is, for example, a polypropylene oxide modified dimethylpolysiloxane although ethylene oxide or mixtures of ethylene oxide and propylene oxide may also be used.

References disclosing suitable silicone fluids include U.S. Pat. No. 2,826,551 to Green; U.S. Pat. No. 3,964,500 to Drakoff; U.S. Pat. No. 4,364,837 to Padner and British Patent No. 849,433 to Woolston. All of these patents are incorporated herein by reference. Also incorporated herein by reference is *Silicon Compounds* distributed by Petrarch Systems, Inc., 1984. This reference provides a very good listing of suitable silicone materials.

Silicone materials found especially useful in the present compositions are silicone gums. Silicone gums described by Petrarch and others including U.S. Pat. No. 4,152,416, May 1, 1979 to Spitzer et al., and Noll, Walter, "Chemistry and Technology of Silicones," Academic Press, New York (1968). Also describing silicone gums are various General Electric Silicone Rubber Product Data Sheets. All of these described references are hereby incorporated herein by reference. "Silicone gum" materials denote high molecular weight polydiorganosiloxanes having a viscosity up to about 50,000,000 cs. Specific examples include polydimethylsiloxane; polydimethylsiloxane; methylvinylsiloxane copolymer; polydimethylsiloxane; diphenylmethylvinylsiloxane copolymer; and mixtures thereof.

As noted above high viscosity polydimethylsiloxanes i.e., those above 100,000 cs are preferred in this invention. Particularly preferred are polydimethylsiloxanes having viscosities ranging from between about 2.5 million cs and about 50 million cs.

The safety of polydimethylsiloxanes for use in these various products is well documented. See Rowe et al., *Journal of Industrial Hygiene*, 30(6): 332–352 (1948). See also Calandra et al., *ACS Polymer Preprints*, 17: 1–4 (1976) and Kennedy et al., *J. Toxicol. & Environmental Health*, 1: 909–920 (1976).

As noted above, the preferred polydimethylsiloxanes useful in the skin care compositions of the present invention are described as polymethylsiloxanes with the chemical composition $(CH_3)_3SiO[SiO(CH_3)_2]_nSi(CH_3)_3$, wherein n is a whole number. These polydimethylsiloxanes have viscosities ranging up to about 50 million cs., and are generally described as having high molecular weight.

The particle size of the silicone in the ULTRAMULSION™ dispersions of the present invention can range from between about 0.1 and about 10 microns. In a preferred embodiment of the present invention the particle size of polydimethylsiloxanes in the ULTRAMULSION™ dispersion ranges from below 1 up to about 5 microns. The particle size distribution of the polydimethylsiloxanes in the ULTRAMULSION™ dispersions of the present invention generally range from between about 80% and about 95% of the particles under 10 microns. See especially FIGS. 4 and 5. In a preferred embodiment of the present invention, from between about 80% and about 95% of the particles are under 5 microns. See also Table 2.

An essential component of the ULTRAMULSION™ dispersion of the present invention is a surfactant. The surfactant, may be selected from any of a wide variety of synthetic anionic, amphoteric, zwitterionic and nonionic surfactants. The surfactants suitable for the purposes of the present invention must function as the continuous phase and contain the discontinuous silicone phase.

Synthetic anionic surfactants can be exemplified by the alkali metal salts of organic sulfuric reaction products having in their molecular structure an alkyl radical containing from 8–22 carbon atoms and a sulfonic acid or sulfuric acid ester radical (NOTE: included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxyl, sulfonate, sulfate, phosphate, or phosphonate. A general formula for these compounds is:

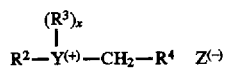

wherein

R$^2$ contains an alkyl, alkenyl, or hydroxyl alkyl radical of from about 8 to 18 carbon atoms, from 0 to about 10 ethylene oxide moieties and from 0 to 1 glyceryl moiety;

Y is selected from the group consisting of nitrogen, phosphorous, and sulfur atoms;

R$^3$ is an alkyl or monohydroxyalkyl group containing 1 to about 3 carbon atoms;

x is 1 when Y is a sulfur atom and 2 when Y is a nitrogen or phosphorous atom;

R$^4$ is an alkylene or hydroxyalkylene of from 1 to about 4 carbon atoms and

Z is a radical selected from the group consisting of carboxylate, sulfonate, sulfate, phosphonate, and phosphate groups.

Examples include:

4-[N,N-di(2-hydroxyethyl)-N-octadecylammonio]-butane-1-carboxylate;

5-(S-3-hydroxypropyl-S-hexadecylsulfonio]-3-hydroxypentane-1-sulfate;

3-[P,P-diethyl-P-3,6,9-trioxatetradecocylphosphonio]-2-hydroxypropane-1-phosphate;

3-[N,N-dipropyl-N-3-dodecoxy-2-hydroxypropylammonio]-propane-1-phosphate;

3-[N,N-dimethyl-N-hexadecylammonio-propane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and 5-(N,N-di(3-hydroxypropyl)-N-hexadecylammonio]-2-hydroxypentane-1-sulfate.

Other zwitterionics such as betaines are also useful in the present invention. Examples of betaines useful herein include the higher alkyl betaines such as cocodimethyl carboxymethyl betaine, lauryl dimethyl carboxymethyl betaine, lauryl dimethyl alpha-carboxyethylene betaine, cetyl dimethyl carboxymethyl betaine, lauryl bis-(2-hydroxyethyl)carboxy methyl betaine, stearyl bis-(2O-hydroxypropyl)-carboxymethyl betaine, oleyl dimethyl gamma-carboxypropyl betaine, lauryl bis-(2-hydroxypropyl)alpha-carboxyethyl betaine, etc. The sulfobetaines may be represented by cocodimethyl sulfopropyl betaine, stearyl dimethyl sulfopropyl betaine, lauryl dimethyl sulfoethyl betaine, lauryl bis-(2-hydroxy-ethyl) sulfopropyl betaine and the like; amido betaines and amidosulfo betaines, wherein the RCONH(CH$_2$)$_3$ radical is attached to the nitrogen atom of the betaine are also useful in this invention. The amido betaines are preferred for use in some of the compositions of this invention. A particularly preferred composition utilizes an amido betaine, a quaternary compound, a silicone, a suspending agent and has a pH of from about 2 to about 4.

Examples of amphoteric surfactants which can be used in the ULTRAMULSION™ dispersions of the present invention are those which can be broadly described as derivatives of aliphatic secondary and tertiary amine in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylamino-propionate, sodium 3-dodecylamino-propane sulfonate, N-alkyltaurines such as the one prepared by reacting dodecylamine with sodium isethionate according to the teachings of U.S. Pat. No. 2,658,072, N-higher alkyl aspartic acids such as those produced according to the teachings of U.S. Pat. No. 2,438,091, and the products sold under the trade name "Miranol" and described in U.S. Pat. No. 2,528,378.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, disobutylene, octane, or nonane, for example.

2. Those derived from the condensation of ethylene oxide with the product resulting from the reaction of propylene oxide and ethylenediamine products which may be varied in composition depending upon the balance between the hydrophobic and hydrophilic elements which is desired. For example, compounds containing from about 40% to about 80% polyoxyethylene by weight and having a molecular weight of from about 5,000 to about 15,000 resulting from the reaction of ethylene oxide groups with a hydrophobic base constituted of the reaction product of ethylene diamine and excess propylene oxide, said base having a molecular weight of the order of 2,500 to 3,000 are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

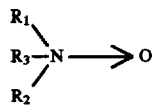

wherein $R_1$ contains an alkyl, alkenyl or monohydroxy alkyl radical of from about 8 to about 18 carbon atoms from 0 to about 10 ethylene oxide moieties, and from 0 to 1 glyceryl moiety, and $R_2$ and $R_3$ contains from 1 to about 3 carbon atoms and from 0 to about 1 hydroxy group, e.g., methyl, ethyl, propyl, hydroxy ethyl, or hydroxypropyl radicals. The arrow in the formula is a conventional representation of a semipolar bond. Example of amine oxides suitable for use in this invention include dimethyl-dodecylamine oxide, oleyldi (2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)tetracylamine oxide, 2-dodecoxyethyldimethylamine oxide, 3-dodecoxy-2-hydroxypropyldi-(3-hydroxy-propyl)amine oxide, dimethylhexadecylamine oxide.

5. Long chain tertiary phosphine oxides corresponding to the following general formula:

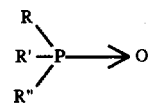

wherein R contains an alkyl, alkenyl or monohydroxyalkyl radical ranging from 8 to 18 carbon atoms in chain length from 0 to about 10 ethylene oxide moieties and from 0 to 1 glyceryl moiety and R' and R" are each alkyl or monohydroxyalkyl groups containing from 1 to 3 carbon atoms. The arrow in the formula is again the conventional representation of a semipolar bond. Examples of suitable phosphine oxides are: dodecyldimethylphosphine oxide, tetradecyldimethylphosphine oxide, tetradecylmethylethylphosphine oxide. 3,6,9-trioxaoctadecyldimethylphosphine oxide, cetyldimethylphosphine oxide, 3-dodecoxy-2-hydroxypropyl-di(2-hydroxyl)phosphine oxide, stearyldimethylphosphine oxide, cetylethylpropylphosphine oxide, cetyldiethylphosphine oxide, dodecyl-diethylphosphine oxide, tetradecyldiethylphosphine oxide, dodecyldipropylphosphine oxide, dodecyldi(2-hydroxyethyl)phosphine oxide, tetradecylmethyl-2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophosphinic chain which contain alkyl, alkenyl, hydroxyalkyl, or keto alkyl radicals containing from about 8 to about 20 carbon atoms, from 0 to about 10 ethylene oxide moieties and from 0 to 1 glyceryl moiety. Examples include octadecyl menthyl sulfoxide, 2-ketotridecyl methyl sulfoxide, 3,6,9,-trioxooctadecyl 2-hydroxyethyl sulfoxide, dodecyl menthyl sulfoxide, oleyl 3-hydroxypropyl sulfoxide, tetradecyl menthyl sulfoxide, 3-methoxytridecyl methyl sulfoxide, 3-hydroxytridecyl methyl sulfoxide, 3-hydroxy-4-dodecoxybutyl methyl sulfoxide.

Many additional nonsoap surfactants are described in McCUTCHEON'S, DETERGENTS AND EMULSIFIERS, 1979 ANNUAL, published by Allured Publishing Corporation which is hereby incorporated herein by reference.

Particularly preferred nonionic surfactants are nonionic poloxamer surfactants of block copolymers of ethylene oxide and propylene oxide ranging from flowable liquids of varying viscosities, to paste, prills and cast solids with molecular weights from 1,100 to 150,000. Suitable nonionic surfactants are manufactured and marketed by BASF Corporation under the trademarks Pluronic. Particularly preferred nonionic surfactants are Pluronic F-68, F-88, F-108 and Pluronic F-127. These are described in a BASF brochure entitled "Pluronic and Tetronic Block Copolymer Surfactant." These nonionic surfactants suitable for the present invention can be described by the following structure:

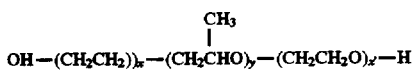

$$OH-(CH_2CH_2)_x-(CH_2CHO)_y-(CH_2CH_2O)_{x'}-H$$

where x, y and x' are whole numbers. Surprisingly, the nonionic surfactants of choice for the ULTRAMULSION™ dispersions of the present invention are reported in the referenced brochure to have marginal detergency, emulsification and wetting properties. See Tables 1 and 2.

As noted above, the preferred nonionic poloxamer surfactants useful in the coating compositions of the present invention are described as polyoxyethylene-polyoxypropylene block copolymers such as Pluronic F-68, F-88, F-108 and F-127 (BASF) which have molecular weights of at least about 1000 such as those described in U.S. Pat. Nos. 4,343,785, 4,465,663, 4,511,563 and 4,476,107, the disclosures of which are hereby incorporated herein by reference.

Emulsions of various coating substances including polydimethylsiloxanes in various surfactants including nonionic surfactants are disclosed and claimed in U.S. Pat. Nos. 4,911,927, 4,942,034; 4,950,479; 5,009,881; 5,032,387; 5,057,306; 5,057,307; 5,057,308, 5,057,309; 5,057,310, 5,098,711, 5,165,913 and 5,284,648. There is however, no teaching or suggestion in these references that these high viscosity silicone emulsions are stable nor that the "coating" substances are oriented as they are in the ULTRAMULSION™ dispersions of the present invention.

The ratio of surfactant to silicone in the ULTRAMULSION™ dispersion coating compositions of the present invention can range from between about 400:1 and about 1:2. In a preferred embodiment of the invention the ratio of surfactant to silicone is from between about 25:1 and 1:2. See Tables 1 and 2.

The ULTRAMULSION™ dispersions of the present invention may be prepared as follows:

Generally, if not a liquid, the surfactant is first heated to a temperature at which it becomes a liquid. The silicone is then dispersed in the heated surfactant with various high shear dispersing means.

In one preferred method, the heated surfactant is mechanically stirred along with the silicone, to form a pre-emulsion mixture in which the silicone is uniformly dispersed in the surfactant in droplets of a larger size than desired for the ULTRAMULSION™ dispersions but small enough to optimize the subsequent high shear dispersions. This mixture is subjected to high-shear dispersions with a means such as the IKA-WORKS DISPAX-Reactor with at least one superfine generator, alternatively, a Ross Model M.E., 100 LC fitted with a 20 mesh screen or a ultrasonicator such as MEDSONIC XL2010 fitted with 800-C Flow Cell & 800-21CT ¾ inch flanged horn can be used.

Various ULTRAMULSION™ dispersions of the present invention are prepared and analyzed as described in detail in the examples below.

PROCEDURE

Examples 1–11 are formed as follows; the Poloxamer is heated to 70°–90° C. to melt the solid material. Once melted, the Poloxamer is stirred with an overhead mixing blade. Dimethicone is added and the entire mass is mixed to obtain a uniform dispersion while maintaining the melt temperature. The material is then transferred to the homogenizer (a ROSS Homogenizer, Model M.E. 100LC), and homogenized for ½ hour at 5000–10,000 RPM. The material is then cooled by a suitable cooling apparatus. The cooled material is then ready for use.

TABLE 1

SKIN CARE

% W/W Example No.

| COMPONENT | 1 | 2 | 3 | 4 | 5 | 6 | 7 | 8 | 9 | 10 | 11 |
|---|---|---|---|---|---|---|---|---|---|---|---|
| DIMETHICONE viscosity-centistokes | | | | | | | | | | | |
| 100,000 | 10 | — | — | — | — | — | — | — | — | 33 | — |
| 600,00 | — | 10 | — | — | — | — | 33 | — | — | — | — |
| 2,500,000 | — | — | 10 | — | — | — | — | 33 | — | — | 10 |
| 4,000,000 | — | — | — | 10 | — | — | — | — | 33 | — | — |
| 30,000,000 | — | — | — | — | 10 | — | — | — | — | — | — |
| 50,000,000 | — | — | — | — | — | 10 | — | — | — | — | — |
| Poloxamer-188 | — | — | — | — | — | — | — | — | — | 67 | — |
| Poloxamer-238 | — | — | — | — | — | — | — | — | — | — | 90 |
| Poloxamer-338 | 90 | 90 | 90 | 90 | 90 | 90 | — | — | — | — | — |
| Poloxamer-407 | — | — | — | — | — | — | 67 | 67 | 67 | — | — |

Specific Poloxamer/polydimethylsiloxane ULTRAMULSION™ dispersions suitable for use with various skin care products were prepared and analyzed as described in Examples 12–17 in Table 2 below:

TABLE 2

SKIN CARE

Example #

| Component | 12 | 13 | 14 | 15 | 16 | 17 |
|---|---|---|---|---|---|---|
| Dimethicone viscosity - centistokes | | | | | | |
| 2,500,000 | 10.0 | — | — | — | 20.0 | — |
| 4,000,000 | — | 10.0 | — | — | — | — |
| 30,000,000 | — | — | 10.0 | — | — | 10.0 |
| 50,000,000 | — | — | — | 10.0 | — | — |
| Poloxamer-338 | 88.0 | 88.0 | 88.0 | 88.0 | 76.0 | 76.0 |
| Poloxamer-407 | | | | | | |
| Salicylic Acid | 2.0 | 2.0 | 2.0 | 2.0 | — | — |
| Octyl Dimethyl PABA | — | — | — | — | 4.0 | 4.0 |

The discontinuous silicone phase of the ULTRAMULSION™ dispersion can also contain a wide range of lipid soluble and/or lipid dispersible skin care ingredients ranging from colorants to essential fragrances such as menthol and camphor to protectants such as U.V. absorbers, to repellents such as N,N.-diethyl-toluamide (DEET) to moisturizers, such as petrolatum, glycerin, etc; to medicinals such as Vitamin E, aloe, etc., to deodorants/antiperspirants such as triclosan, aluminum zirconium trichlorohydrex gly, etc.; to antimicrobials such as triclosan; to antiseptics such as benzalkonium chloride, etc.; to antihistamines such as diphenylhydramine hydrochloride; to seborrheic dermatitis as psoriasis actives such as coal tar and steroids to analgesics such as benzocaine, lidocaine, etc.

These various ingredients are contained at least to some extent in the silicone phase of the ULTRAMULSION™ dispersion to perform various skin functions as though they are contained in a "reservoir" as they continue to be available at the ULTRAMULSION™ skin care interface, as long as the ULTRAMULSION™ dispersion coating remains substantive to the skin. The sustained moisturizing, protecting, healing, etc. effects on skin obtained with these improved skin care products are discussed in various examples below.

The skin care products containing the ULTRAMULSION™ dispersions of the present invention will contain a variety of essential components ranging from surfactants for cleaning, to various moisturizing substances. These are detailed in various Examples described below.

Water is an essential component of most skin care products of the present invention which contain one or more of the various ULTRAMULSION™ dispersions described above. The water in these products is generally present at a level of from about 20% to about 95%, preferably from between about 60% and about 90%.

In addition these skin care products can contain a variety of nonessential optional components suitable for rendering such compositions more cosmetically acceptable. See Tables 3 to 6 below.

Such conventional optional ingredients are well known to those skilled in the art, e.g., preservatives such as benzyl alcohol, methyl paraben, propyl paraben and imidizolidinyl urea; cationic surfactants such as cetyl trimethylammonium chloride, lauryl trimethyl ammonium chloride, tricetyl methyl ammonium chloride, stearyldimethyl benzyl ammonium chloride, and di(partially hydrogenated tallow) dimethylammonium chloride; thickeners and viscosity modifiers such as diethanolamide of a long chain fatty acid (e.g., PEG 3 lauramide), block polymers of ethylene oxide and propylene oxide such as Pluronic F88 offered by BASF Wyandotte, sodium chloride, sodium sulfate, polyvinyl alcohol, and ethyl alcohol; pH adjusting agents such as citric acid, succinic acid, phosphoric acid, sodium hydroxide, sodium carbonate, etc., perfumes; dyes; and, sequestering agents such as disodium ethylenediamine tetraacetate. Such agents generally are used individually at a level of from about 0.01% to about 10%, preferably from about 0.5% to about 5.0% by weight of the composition.

The pH of the present compositions is not critical and may be in the range of from 2 to about 10. However, as set forth earlier certain zwitterionic/quaternary compositions preferably have pH's of from about 2 to about 4.

METHOD OF MANUFACTURE

The skin treatment products of the present invention can be made by mixing the materials together and heating to about 72° C. The mixture is mixed thoroughly for about 10 minutes at the 72° C. temperature before being pumped through a heat exchanger to cool it to about 27° C.

INDUSTRIAL APPLICABILITY

The skin treatment ULTRAMULSION™ dispersions of the present invention are used in a conventional manner in various cosmetic, OTC Drug and ℞ drug products for cleaning, moisturizing, coloring, protecting, treating, healing etc. the skin, as shown in the Examples and Tables below.

The following Examples further describe and demonstrate preferred embodiments within the scope of the present invention. The Examples are given solely for the purpose of illustration and are not to be construed as limitations of the present invention as many variations thereof are possible without departing from its spirit and scope.

The following compositions are illustrative of skin care products of the present invention that are used routinely to capitalize on the substantivity, coating efficiency and "reservoir" effect characteristic of ULTRAMULSION™ dispersions.

Various skin moisturizers, facial cleansers, an acne scrub and hand/face liquid detergent formulations of the present invention are described in Examples 18 to 29 in Tables 3–6 below.

TABLE 3

SKIN MOISTURIZERS

% W/W Example #

| Component | 18 | 19 | 20 | 21 | 22 |
|---|---|---|---|---|---|
| Phase A | | | | | |
| Glyceryl Stearate (and) PEG 100 Stearate | 2.0 | 2.0 | 2.0 | 2.0 | 2.0 |
| Stearyl Alcohol | 1.0 | 1.0 | 1.0 | 1.0 | 1.0 |
| Stearic Acid | 2.5 | 2.5 | 2.5 | 2.5 | 2.5 |
| Diocetylisostearate | 4.5 | 4.5 | 4.5 | 4.5 | 4.5 |
| Phase B | | | | | |
| Water and Carbopol 940 | 0.3 | 0.3 | 0.3 | 0.3 | 0.3 |
| Phase C ULTRAMULSION™ From: | | | | | |
| Example 2 | 3.0 | — | — | — | — |
| Example 3 | — | 3.0 | — | — | — |
| Example 5 | — | — | 3.0 | — | — |
| Example 8 | — | — | — | 3.0 | — |
| Example 15 | — | — | — | — | 3.0 |
| Phase D | | | | | |
| Triethanolamine | 0.5 | 0.5 | 0.5 | 0.5 | 0.5 |
| Phase E | | | | | |
| Preservatives | Q.V. | Q.V. | Q.V. | Q.V. | Q.V. |
| Fragrance | Q.V. | Q.V. | Q.V. | Q.V. | Q.V. |

TABLE 4

FACIAL CLEANSER

% W/W Example #

| Component | 23 | 24 | 25 |
|---|---|---|---|
| Disodium Cocoamphodiacetate | 12.0 | 12.0 | 12.0 |
| Sodium Lauryl Sarcosinate | 10.0 | 10.0 | 10.0 |
| Cocoamidopropyl Beatine | 7.0 | 7.0 | 7.0 |
| Lauriamide DEA | 4.0 | 4.0 | 4.0 |
| Water | 62.5 | 63.5 | 63.5 |
| Citric Acid | 0.5 | 0.5 | 0.5 |
| ULTRAMULSION™ From: | | | |
| Example 6 | 4.0 | — | — |
| Example 4 | — | 3.0 | — |
| Example 10 | — | — | 3.0 |
| Preservative | Q.V. | Q.V. | Q.V. |
| Fragrance | Q.V. | Q.V. | Q.V. |

TABLE 5

ACNE SCRUB % W/W

| Component | Example 26 |
|---|---|
| Water | 73.3 |
| Sodium $C_{14}$–$C_{16}$ Olefin Sulfonate | 16.0 |
| Cocoamide propyl Beatine | 2.0 |
| Sodium $C_{12}$–$C_{15}$ Pureth Sulfonate | 4.0 |
| Aloe Vera Extract | 0.1 |
| ULTRAMULSION™ from Example 15 | 4.0 |
| Sodium Chloride | 0.6 |

TABLE 5-continued

ACNE SCRUB % W/W

| Component | Example 26 |
|---|---|
| Fragrance | Q.V. |
| Preservative | Q.V. |

TABLE 6

HAND AND FACE LIQUID DETERGENT % W/W

| | Example # | | |
|---|---|---|---|
| Component | 27 | 28 | 29 |
| Water | 62.9 | 62.9 | 62.9 |
| Sodium Lauryl Sulfate | 25.0 | 25.0 | 25.0] |
| Sodium Laureth Sulfate | 6.0 | 6.0 | 6.0 |
| Cocamidopropyl Betaine | 3.0 | 3.0 | 3.0 |
| Glyceryl Cocoate | 2.0 | 2.0 | 2.0 |
| EDTA | 0.5 | 0.5 | 0.5 |
| Sodium Chloride | 0.6 | 0.6 | 0.6 |
| Preservative | Q.V. | Q.V. | Q.V. |
| Fragrance | Q.V. | Q.V. | Q.V. |
| ULTRAMULSION ™ from: | | | |
| Example 1 | 3.0 | — | — |
| Example 4 | — | 3.0 | — |
| Example 17 | — | — | 3.0 |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A skin care composition comprising an aqueous-free high shear dispersion, formed by heating a mixture of surfactant and silicone, followed by high shear mixing wherein:

a. the silicone is insoluble in said surfactant, has a viscosity within the range of from about 2.5 million cs to about 50 million cs, and a particle size from between about 0.1 and about 10 microns;

b. the surfactant to silicone ratio in the high shear dispersion is from between about 400:1 and about 1:2; and the surfactant has an orienting effect on the silicone, c. the high shear dispersion forms stable dispersions in aqueous based skin care compositions, and d. wherein said skin care compositions exhibit enhanced substantivity to skin while the dispersed silicone phase of said high shear dispersion functions as a reservoir for additional lipid soluble and lipid dispersible skin treatment ingredients.

2. A skin care composition according to claim 1, wherein said high shear dispersion comprises a surfactant and polydimethylsiloxane wherein:

a. said polydimethylsiloxane has the chemical formula $(CH_3)_3SiO[SiO(CH_3)_2]_nSi(CH_3)_3$, wherein n is a whole number;

b. said polydimethylsiloxane contains a lipid soluble active ingredient;

c. the viscosity of the polydimethylsiloxane ranges from between about 2.5 million and about 4 million cs;

d. the particle size of at least 90% of the polydimethylsiloxane in the high shear dispersion is from between about 0.5 and about 10 microns;

e. in terms of particle size distribution, from between about 80% and about 95% of the particles are under 5 microns;

f. the ratio of surfactant to polydimethylsiloxane is from between about 400:1 and about 1:1; and g. the high shear dispersion, when dispersed in water based skin care compositions, is stable therein.

3. A skin care composition according to claim 1, wherein the ratio of said surfactant to said silicone is 1:1 and the silicone particles in said high shear dispersion are less than 10 microns.

4. A skin care composition according to claim 1, wherein the ratio of said surfactant to said silicone is 9:1 and 90% of the silicone particles are from between about 1 and 3 microns.

5. A skin care composition according to claim 1, wherein the ratio of said surfactant to said silicone is 2:1 and the particle size of 100% of the silicone dispersion is less than 10 microns.

6. A skin care composition according to claim 1, wherein the silicone is a polydimethylsiloxane, uncoiled and oriented, and wherein the oxygen moieties are generally oriented in a plane distinct from that of the methyl moieties.

7. A skin care composition according to claim 1, wherein the physical state of the surfactant is selected from the group consisting of flowable liquids, pastes, prills and cast solids.

* * * * *